US006102920A

United States Patent [19]
Sullivan et al.

[11] Patent Number: 6,102,920
[45] Date of Patent: Aug. 15, 2000

[54] NEEDLE GRASPING APPARATUS

[75] Inventors: Roy H. Sullivan, Uxbridge; Barry N. Gellman, North Easton, both of Mass.

[73] Assignee: Boston Scientific Corporation, Natick, Mass.

[21] Appl. No.: 09/010,988

[22] Filed: Jan. 22, 1998

Related U.S. Application Data

[63] Continuation of application No. 08/645,173, May 13, 1996, Pat. No. 5,746,753.

[51] Int. Cl.$^7$ ................................................. A61B 17/04
[52] U.S. Cl. ............................................ 606/147; 606/148
[58] Field of Search ..................... 606/147, 144, 606/148, 139

[56] References Cited

U.S. PATENT DOCUMENTS

| | | |
|---|---|---|
| 2,363,334 | 11/1944 | Jones ........................................ 606/144 |
| 3,878,848 | 4/1975 | Hiebert . |
| 4,109,658 | 8/1978 | Hughes . |
| 4,446,866 | 5/1984 | Davison . |
| 4,491,135 | 1/1985 | Klein . |
| 4,597,390 | 7/1986 | Mulhollan et al. . |
| 4,621,640 | 11/1986 | Mulhollan et al. . |
| 4,793,349 | 12/1988 | Weinrib . |
| 4,800,880 | 1/1989 | Catalano . |
| 4,815,476 | 3/1989 | Clossick .................................. 128/751 |
| 4,872,458 | 10/1989 | Kanehira et al. . |
| 5,015,250 | 5/1991 | Foster ...................................... 606/147 |
| 5,181,919 | 1/1993 | Bergman et al. . |
| 5,201,744 | 4/1993 | Jones . |
| 5,222,962 | 6/1993 | Burkhart . |
| 5,259,366 | 11/1993 | Reydel et al. . |
| 5,281,236 | 1/1994 | Bagnato et al. . |
| 5,300,082 | 4/1994 | Sharpe et al. . |
| 5,304,185 | 4/1994 | Taylor . |
| 5,312,351 | 5/1994 | Gerrone . |
| 5,312,422 | 5/1994 | Trott . |
| 5,320,608 | 6/1994 | Gerrone . |
| 5,336,230 | 8/1994 | Leichtling et al. . |
| 5,356,416 | 10/1994 | Chu et al. . |
| 5,364,409 | 11/1994 | Kuwabara et al. . |
| 5,376,096 | 12/1994 | Foster . |
| 5,391,174 | 2/1995 | Weston . |
| 5,391,176 | 2/1995 | de la Torre . |
| 5,413,583 | 5/1995 | Wohlers . |
| 5,437,682 | 8/1995 | Grice et al. . |
| 5,447,512 | 9/1995 | Wilson et al. . |
| 5,448,989 | 9/1995 | Heckele . |
| 5,454,819 | 10/1995 | Knoepfler ................................ 606/147 |
| 5,483,951 | 1/1996 | Frassica et al. . |
| 5,601,578 | 2/1997 | Murphy ................................... 606/148 |
| 5,643,289 | 7/1997 | Sauer et al. ............................. 606/139 |
| 5,676,678 | 10/1997 | Schad ...................................... 606/170 |
| 5,766,184 | 6/1998 | Matsuno et al. ........................ 606/142 |

*Primary Examiner*—Michael Buiz
*Assistant Examiner*—Julian W. Woo
*Attorney, Agent, or Firm*—Finnegan, Henderson, Farabow, Garrett & Dunner, L.L.P.

[57] ABSTRACT

Apparatus for needle grasping and performing a second modality comprising a sheath axially extending between distal and proximal ends thereof. The device includes an inner hollow tube with a slot formed therein for receiving a needle at the distal end. Retraction and extension of the inner tubular member relative to the sheath enable the grasping and releasing of a suture needle received in the slot. A handle is provided at the proximal end of the apparatus for selectively extending and retracting the inner tube relative to the sheath and for retaining the inner tube in its extended and retracted positions. A second switch can be provided in the handle to actuate a catheter slidably inserted through the inner tube to perform a second therapeutic modality. The catheter preferably includes a distal bight that forms a loop when extended from the distal end of the sheath for facilitating intracorporeal knot tying thereat. The catheter includes a lumen therethrough for receiving suture thread for use at the distal end of the sheath.

41 Claims, 9 Drawing Sheets

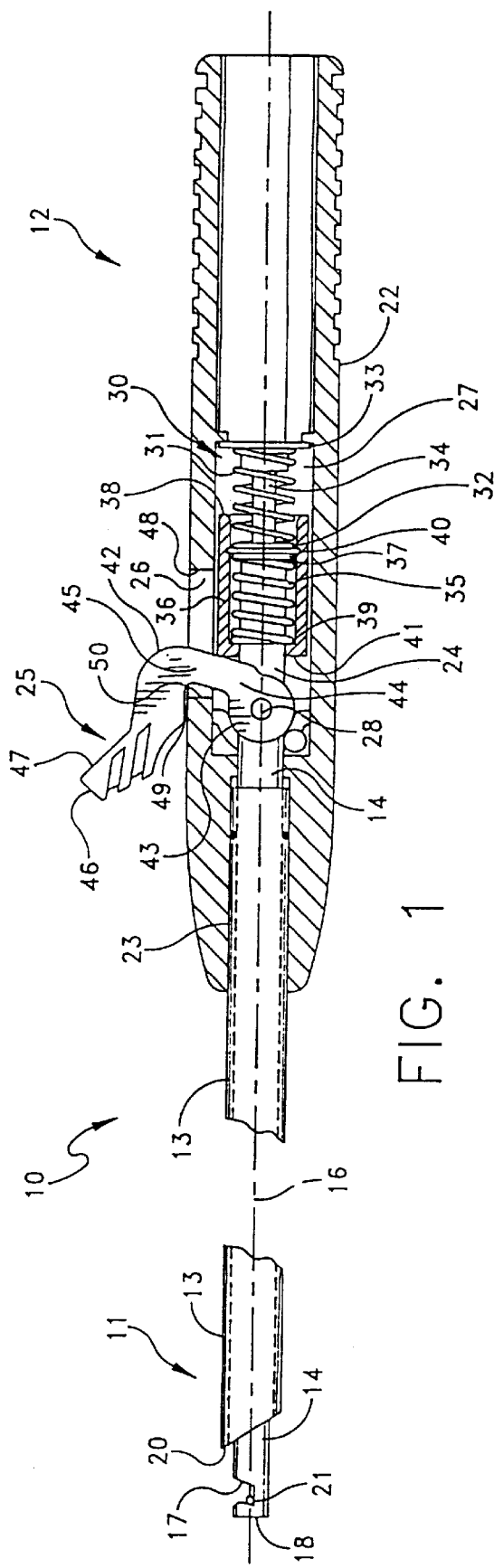
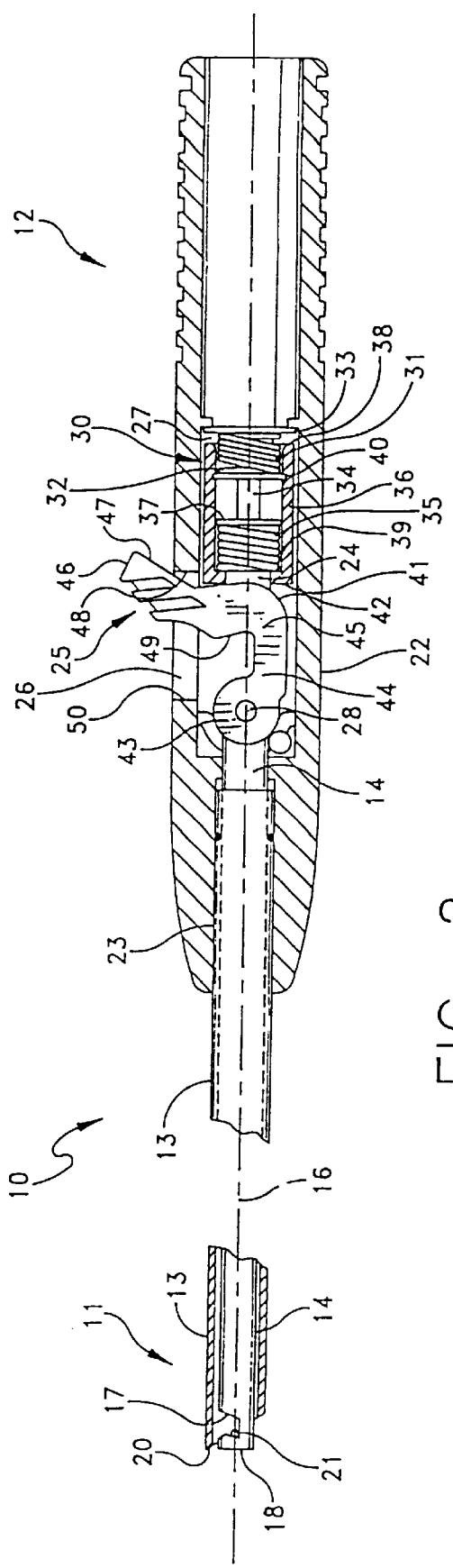
FIG. 1
FIG. 2

NEEDLE GRASPING APPARATUS

This is a continuation of application Ser. No. 08/645,173 filed May 13, 1996, now U.S. Pat. No. 5,746,753, which is incorporated herein by reference.

BACKGROUND OF THE INVENTION

1. Field of the Invention

This invention relates to surgical devices and procedures and more specifically to an apparatus for suturing openings in a patient during endoscopic surgical procedures.

2. Description of Related Art

In endoscopic surgical procedures, all the techniques of dissection and suturing, including knot tying, must be performed with various elongated instruments that extend through trocars into a cavity of a patient. These instruments generally include needle holders, tissue graspers, introducers and related instruments for facilitating both extracorporeal and intracorporeal knot tying and suturing during endoscopic surgical procedures. During such endoscopic surgical procedures the needle holders and knot tying devices are generally among the final devices to inserted into and removed from the trocars to suture the patient's tissue.

The following United States Letters Patent disclose representative needle gripping and driving apparatus for use during endoscopic surgical procedures:

| | |
|---|---|
| 3,878,848 | (1975) Hiebert |
| 5,015,250 | (1991) Foster |
| 5,300,082 | (1994) Sharpe et al. |
| 5,312,422 | (1994) Trott |
| 5,364,409 | (1994) Kuwabara et al. |
| 5,376,096 | (1994) Foster |

U.S. Pat. No. 3,878,848 to Hiebert discloses a needle capturing device. This device includes a handle member at one end and a tip in the form of a solid block which may be penetrated by a surgical needle so that manipulation of the handle member permits manipulation of the suture needle penetrating the block.

U.S. Pat. No. 5,015,250 to Foster discloses a needle driver for selectively grasping a suture needle. A cross-channel in an overlying sheath receives the suture needle. A distal end of a slidable inner rod supported within the sheath grips the needle by distally pushing it against a wall of the cross-channel. Proximal manipulation of a handle portion supported at a proximal end of the sheath and the inner rod enables retraction and extension of a distal end of a inner rod relative to the channel for selectively grasping and releasing the suture needle.

U.S. Pat. No. 5,300,082 to Sharpe et al. discloses a surgical instrument having a trigger handle for grasping a needle at a distal end of a tubular member. The distal end includes a cross-notch or channel for receiving the needle whereby an end of the inner tube clamps the needle against a distal end of the notch. The trigger handle includes a latching device that selectively locks the needle members in position when the needle is engaged.

U.S. Pat. No. 5,312,422 to Trott discloses a suturing needle apparatus that includes an elongated handle with a push block that connects with a slide actuated thumb switch. The push block also connects with an elongated needle assembly that extends distally from the handle. The distal end of the needle portion is selectably retractable relative to a distal end of an overlying sheath member to retain a suture in a slot of the needle. A finger switch overcomes a lock feature that inhibits unintended extension of the needle assembly.

U.S. Pat. No. 5,364,409 to Kuwabara et al. discloses a needle holder for gripping a needle within a body cavity. The disclosed device includes an elongated tubular member underlying a sheath. A fixed needle holding element and a movable holding element support at a distal end of the tubular member come together with the fixed element in a scissors-like fashion to grip a needle. An inner core extending from a biased scissors-like handle slides in the tubular member responsive to manipulation of the handle to actuate the movable holding element between the gripping and released positions. The outer surface of the tubular member also includes a suture hook or fixing element to assist in the formation of loops for tying the suture in an overhand knot.

U.S. Pat. No. 5,376,096 to Foster discloses a needle driver for selectively grasping a suture needle. A channel in a distal end of a slidable inner rod supported within an overlying sheath grips the needle in the channel against a distal end of an overlying sheath. Manipulation of a handle portion supported at a proximal end of the sheath and inner rod enables retraction and extension of the inner rod relative to the sheath for selectively grasping and releasing the suture needle.

The following United States Letters Patent disclose representative apparatus for intracorporeal knot tying in endoscopic surgical procedures:

| | |
|---|---|
| 5,281,236 | (1994) Bagnato et al. |
| 5,336,230 | (1994) Leichtling et al. |
| 5,391,176 | (1995) de la Torre et al. |
| 5,447,512 | (1995) Wilson et al. |

U.S. Pat. No. 5,281,236 to Bagnato et al. discloses a method and device for intracorporeal knot tying. The device includes a proximal control apparatus, a distally extending, axially stiff sheath, and a distally extending tubular member formed of shaped memory material for carrying a suture thread through a through passage in the tubular member. The tubular member includes a bight formed of a shape memory material at its distal end that upon selective extension from the sheath forms a loop and upon retraction into the sheath returns to a linear extension. When the tubular member is extended from the sheath and a free end of the suture material extends through the tubular member is passed through the loop, retracting the tubular member forms an overhand knot: in the suture material. Subsequent tightening of the knot is performed by pulling the suture material proximally through the tubular member while grasping with a grasping device the free end of the suture material.

U.S. Pat. No. 5,336,230 to Leichtling et al. discloses an endoscopic suture tying apparatus that includes a proximal operating section with scissors-like members for external manipulation by a surgeon to control a distal section extending internally of a patient. The distal section comprises first and second hollow tube members having a bore therein and a push/pull rod slidably mounted in the bore of each of the tubular members. The scissors-like member secures to the proximal end of each of the tube members for selectively moving the push/pull rods. The ends of the tube are used to selectively loop suture material and pull the suture material through the loops to knot the suture material.

U.S. Pat. No. 5,391,176 to de la Torre et al. discloses a surgical instrument and method for tying knots in a length of suture material at a remote location. The device includes a hollow tube with suture threads wrapped in axially spaced loops proximate a distal end of the tube. A proximally extending slot at the distal end of the tube underlies the spaced loops. Passing a suture needle secured to the free end of the suture material into the distal end of the tube and out of the slot proximally of the distal most loop forms an overhand knot in the suture material.

U.S. Pat. No. 5,447,512 to Wilson et al. discloses an intracorporeal knot tying device with a proximal controller or handle and a distal portion substantially identical to the distal portion of the device disclosed by U.S. Pat. No. 5,281,236 to Bagnato et al., as described above. The controller includes a housing that supports a slide button for selectively extending and retracting the tubular member relative to the sheath. The slide button also enables the user to engage the suture material as the slide button retracts the tubular member so as to pull one side of an intercorporeal knot formed proximate a distal end of the tubular member.

The foregoing references disclose various apparatus for gripping and driving needles during intracorporeal knot tying. However, they fail to disclose a singular apparatus that enables grasping and driving a needle in order to suture a patient's tissue and that facilitates intracorporeal knot tying to secure the suture. The apparatus disclosed by these references also fail to provide an easily used control apparatus that holds needle grasping members in open and closed positions to positively grasp and release a suture needle when selectively moved to such positions. Further, the references fail to teach a device with a needle grasping apparatus at a distal end and a proximal operating apparatus that controls both the needle graspers and a second catheter extending distally in the device for providing alternative or additional therapeutic modalities of treatment.

SUMMARY

Therefore it is an object of this invention to provide a method and an apparatus for positively retaining suture needle grasping members of the apparatus in selected open and closed positions.

It is another object of this invention to provide needle grasping apparatus that can be used to perform a second modality of therapeutic treatment.

It is yet another object of this invention to provide a needle grasping apparatus that includes a handle for selectively and positively urging grasping members of the apparatus to open and closed positions.

It is still another object of this invention to provide a method and an apparatus for positively and selectively grasping and releasing a suture needle and for performing a second therapeutic procedure. It is yet still another object of this invention to provide a proximal handle for a needle grasping apparatus that selectively retains distal grasping members of the apparatus in selected open and closed positions and that selectively extends a tubular member relative to the grasping members for performing a second procedure.

It is a further object of this invention to provide a method and apparatus for suturing a patient's tissue with a needle grasping and driving device and facilitating intracorporeal knot tying with the same device.

Accordingly apparatus for facilitating endoscopic therapy according to this invention includes first and second coaxially extending members that are displacable between first and second end positions relative to one another with an intermediate position defined in response to interference between end portions of the coaxial members. A handle attaches to the proximal end portion of the first coaxial member and supports a camming member for moving the coaxial members between first and second positions. A lost motion transfer unit coaxially mounts with the coaxial members and abuts the housing, camming member and the second coaxial member. The lost motion transfer unit responds to motion of the camming member by establishing a first end position when the camming member is in a first position. When the camming member moves to a second position, the lost motion transfer unit establishes the second end position and the intermediate position depending upon the presence of interference at the distal end portions of the coaxial members.

In accordance with another aspect of this invention a needle grasping apparatus with proximal and distal ends for facilitating intercorporeal knot tying of suture material during endoscopic procedures includes first and second grippers proximate a distal end of the apparatus, a catheter extending between the proximal and distal end of the apparatus, and a controller at the proximal end for operating the catheter and the first and second grippers. One of the grippers includes a proximally extending portion. The controller includes a housing that supports a cam member for movement between first and second positions and a cam follower axially displaced from the cam member. A first biasing member of the controller engages the housing and the cam follower and urges the cam follower towards the camming member. A second biasing member of the controller extending between a proximal end of the one gripper and the cam follower urges the cam follower away from the proximal end of the one gripper. The first biasing member thus compresses in response to the motion of the camming member and the second biasing member compresses in response to motion of the camming member when interference exists between the first and second grippers.

BRIEF DESCRIPTION OF THE DRAWINGS

It is intended that the appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 1 is a side view in cross section of a needle grasping apparatus according to this invention with a needle gripping member in an extended position for releasing a suture needle;

FIG. 2 is a side view in cross section of a needle grasping apparatus of FIG. 1 with the needle gripping member in an intermediate position for retaining the suture needle;

DESCRIPTION OF ILLUSTRATIVE EMBODIMENTS

Figure 3:
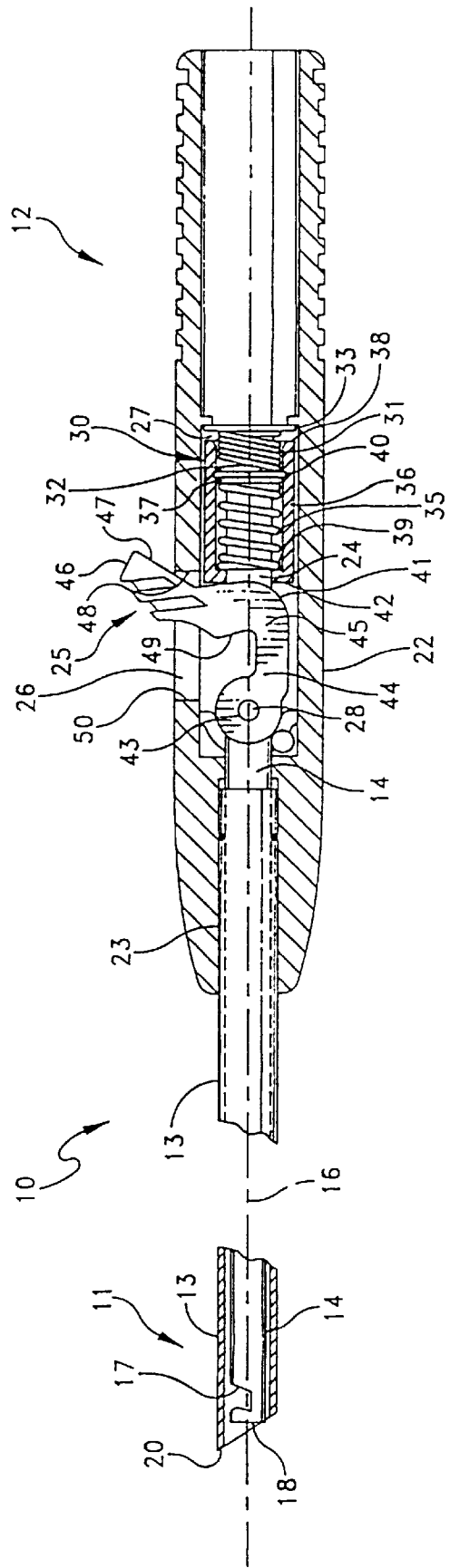
FIG. 3 is a side view in cross section of the needle grasping apparatus of FIG. 1 with the needle gripping member in a fully retracted position without a suture needle.

An apparatus 10 for facilitating intracorporeal suturing of a patient's tissue according to this invention as depicted in FIG. 1 comprises distal and proximal sections 11 and 12, respectively. The distal section 11 includes a sheath 13 and a tubular member 14, each of which extends generally along an axis 16. A transverse slot 17 proximate a distal end 18 of the tubular member 14 and a distal end of the sheath 13 define needle grasping members that, upon relative axial displacement of the tubular member 14 and the sheath 13, operate to release and to grip a suture needle 21 disposed in the slot 17. That is, distal axial displacement of the tubular member 14 relative to the sheath 13 releases the needle 21 as depicted in FIG. 1 where the tubular member 14 is shown in a distally extended position. Proximal displacement either causes the needle 21 to be clamped at the distal end 18 as depicted in FIG. 2 in an intermediate clamping position or causes the tubular member 14 to displace to a proximally retracted position within the sheath 13 as depicted in FIG. 3 if no needle is in slot 17.

Figure 4:
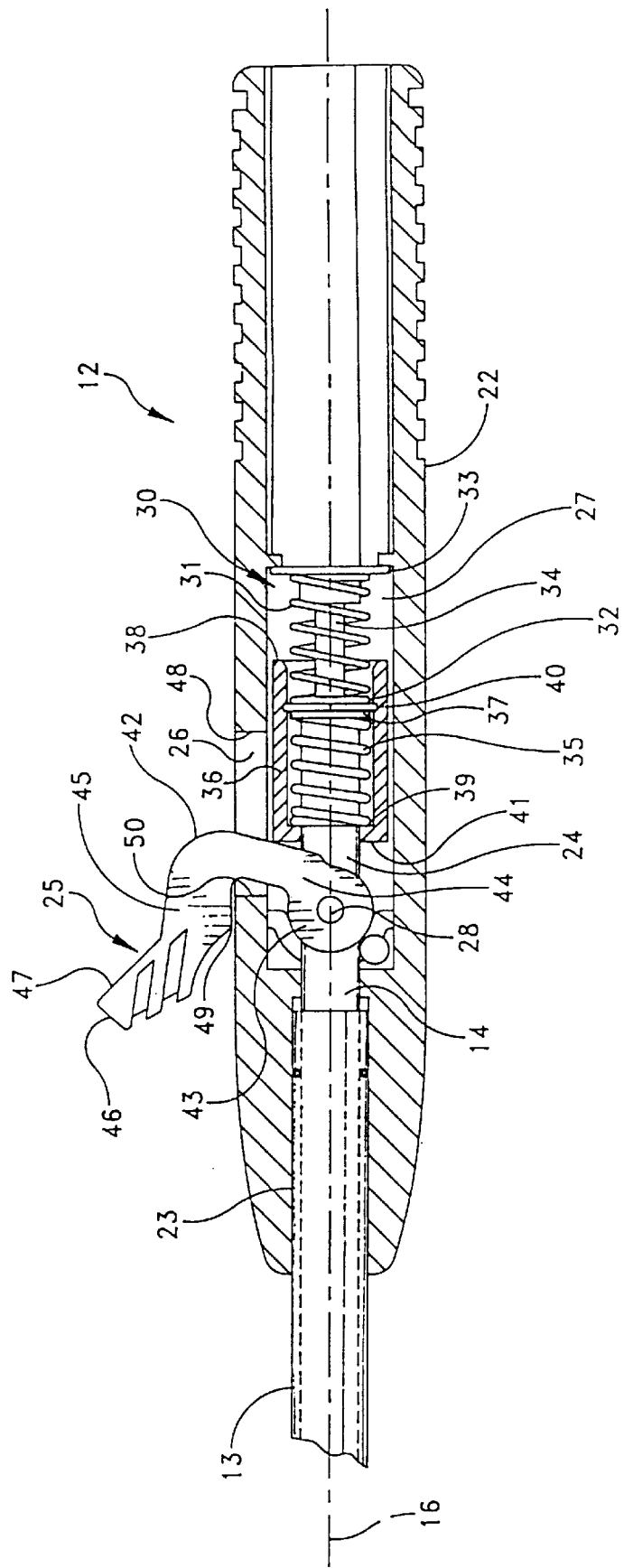
FIG. 4 is an enlarged side view of a handle used in the needle grasping apparatus of FIGS. 1 through 3.

At the proximal section 12 shown in FIGS. 1 through 3, and in an enlarged form in FIG. 4, a handle 22 attaches to a proximal end 23 of the sheath 13 as a first co-axial member and supports a proximal end 24 of the second tubular member 14 as a second co-axial member to enable displacement relative to the sheath 13. The second tubular member 14 thereby can move to its distally extended, proximally retracted or intermediate needle clamping positions. A lever switch or trigger 25 extends through a slot or passage 26 from a cavity 27 in the handle 22. The trigger mounts for rotation on transverse axles or bosses 28 within the housing 27 for movement between first and second limit positions as seen in FIGS. 1 and 2, respectively.

A lost motion transfer assembly 30 enables the two positions of the trigger to translate the tubular member 14 to any of its three positions in a positive fashion. That is, when the trigger is in its fully clockwise position as shown in FIGS. 2 and 3, the inner tubular member 14 will be in its clamping position if a needle 21 is positioned at the distal end thereby to cause interference between the co-axial members or in its fully retracted position if no needle is present. When the trigger is moved counter clockwise to the position shown in FIG. 1, the inner tubular member 14 is in its distally extended position.

Referring specifically to FIG. 4, the lost motion transfer assembly 30 includes a first spring member 31, a central transverse annular flange 32 and a proximal flange 33 that abut the distal and proximal ends of the first spring member 31 respectively, a guide tube 34, a second spring member 35 and a casing in the form a spring cup 36 positioned to abut the proximal end of the second spring member 35. A flange 37 is formed integrally with the proximal end of the inner tubular member 14. More specifically, the first spring member 31 is co-axially positioned over the guide tube 34 and biases the flange 32 distally away from the tubular flange 33. The guide tube 34 extends into the tubular member 14 to maintain the proximal end 24 on the axis 16 during translation of the tubular member 14. The second spring member 25 is co-axial with the proximal end 24.

The spring cup 36 or casing has a cylindrical shape with an open proximal end 38 and a partially closed distal end 39 that is adapted to slide over the proximal end 24 of the inner tubular member 14. The edge of a flange 40 engages an inner groove in the spring cup 36 displaced slightly proximally from the proximal end 38. The spring 35 thus lies between the distal end 39 of the spring cup 36 and the flange 37. Moreover the spring 31 has a lower modulus than the spring 35.

The distal end 39 of the spring cup 36 or casing is formed with an oblique or skewed transverse surface 41 that interacts with a camming surface 42 on the trigger 25. The trigger has a mounting base portion 43 that rides on the axle 28 and may be further captured and supported by a saddle 44. Typically the trigger base portion 43 will have two spaced mounting portions that straddle the inner tubular member 14. An arm structure 45 that may comprise a common arm or spaced arm portions, extends from the base portion 43 through the slot 26. An actuator or manipulator 46 in the form of a thumb actuator in FIG. 4 enables the displacement of the trigger between its first and second positions.

In this particular embodiment, interference between a surface 47 on the trigger and an outer surface 48 of the handle 22 adjacent the distal end of the slot 26 produces a positive stop or limit for clockwise motion of the trigger 25. Interference between a surface 49 on the trigger and a surface 50 on the handle adjacent the proximal end of the slot 26 produces a positive stop or limit for counter clockwise motion of the trigger 25.

Referring now to FIGS. 1 and 4, when the trigger is in its fully counter clockwise position, the spring 31 drives the flange 32 distally to displace the distal end 39 of the spring cup 36 against the camming surface 42. Simultaneously the spring 35 drives the flange 37 and the inner tube 14 proximally until the flange 37 abuts the flange 40. This defines the distally extended position of the inner tubular member 14.

If a suture needle is positioned at the distal end 11 as shown in FIG. 2, a two-phase operation results as the trigger moves to the clockwise stop. Initially no interference exists between the inner tubular member 14 and the sheath 13 so the spring cup 36 moves proximally and compresses the spring 31. The spring 35, due to its higher modulus, remains as shown in FIGS. 1 and 4. When the inner tubular member 14 closes on the suture needle 21, no additional proximal motion of the inner tubular member 14 can occur. As the trigger continues to rotate to the positive stop for clockwise motion, it continues to displace the spring cup 36 in the lost motion transfer assembly 30 and now compresses the spring 31 and begins to compress the spring 35 as the flange 37 remains stationary. When the trigger reaches the positive clockwise stop, both the springs 31 and 35 are fully compressed, the trigger 25 is in a stable position and the spring 35 produces the clamping force on the suture needle at the distal end of the device. This constitutes an intermediate clamping position.

If no suture needle is present, the trigger 25 moves to the position in FIG. 3. In this position only the spring 31 compresses fully. The spring 35 fully separates the end 41 of the spring cup 36 and the flange 32. The springs 31 and 35 cooperate to urge the skewed surface 41 of the spring cup 36 to bear continuously on the camming surface 42. The camming surface 42 when in each of counter clockwise and clockwise positions is in an over-center position. That is, in FIG. 1 the spring 31 acts to drive the trigger against the counterclockwise stop; in FIGS. 2 and 3, the springs 31 and 35 drive the trigger against the clockwise stop. Consequently no operator force is needed to maintain the trigger 25 in either of these positions.

Figure 5:
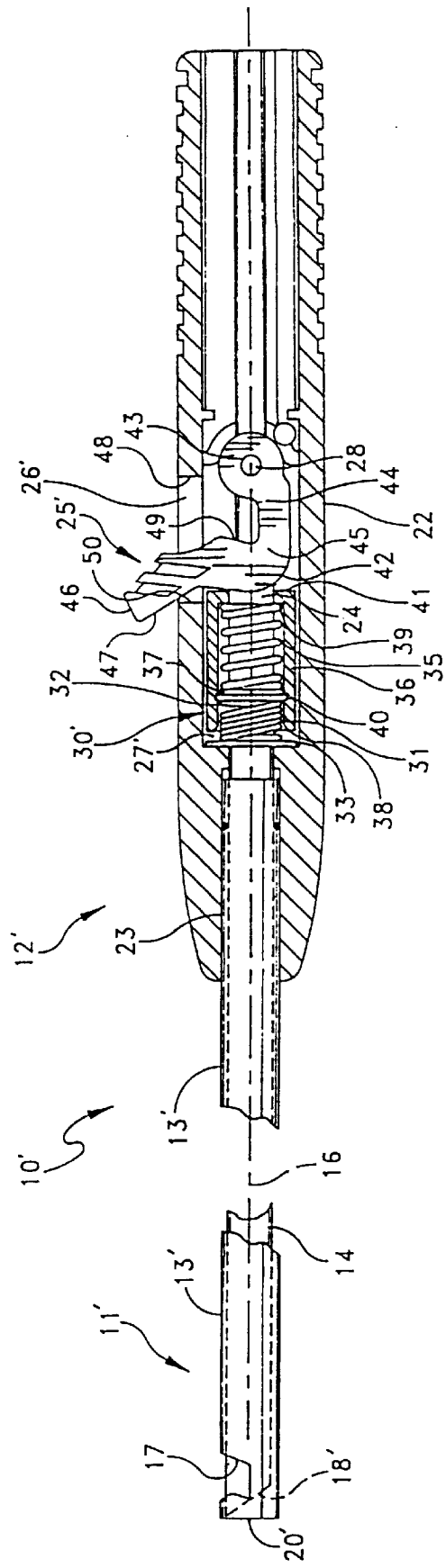
FIGS. 5 through 7 are views of an alternative embodiment of this invention corresponding to FIGS. 1 through 3.
Figure 6:
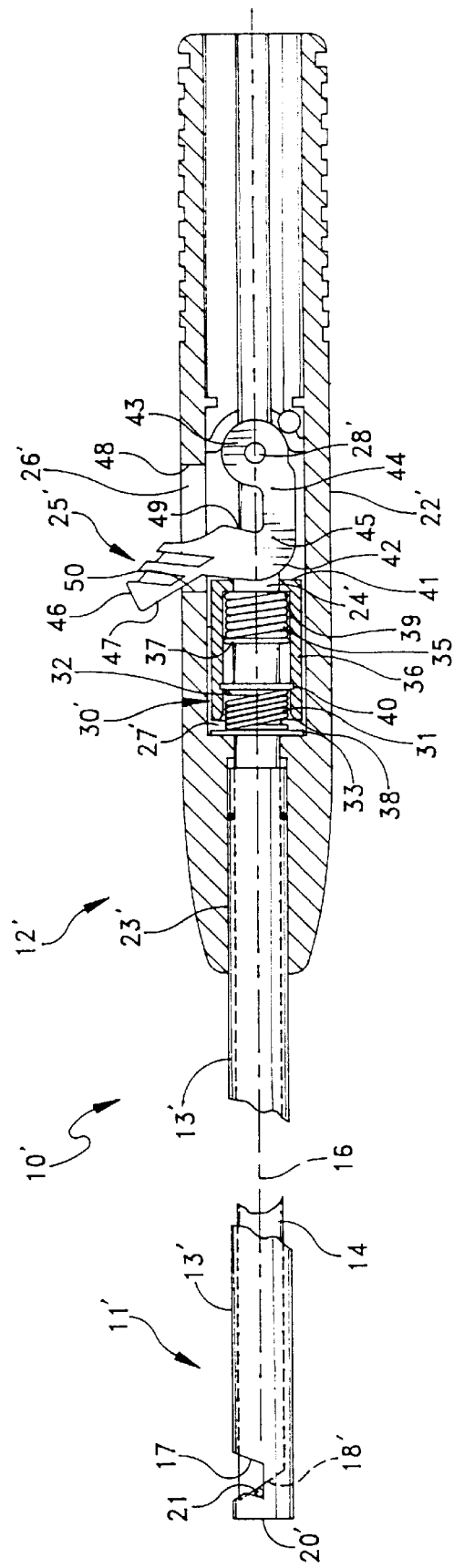
Figure 7:
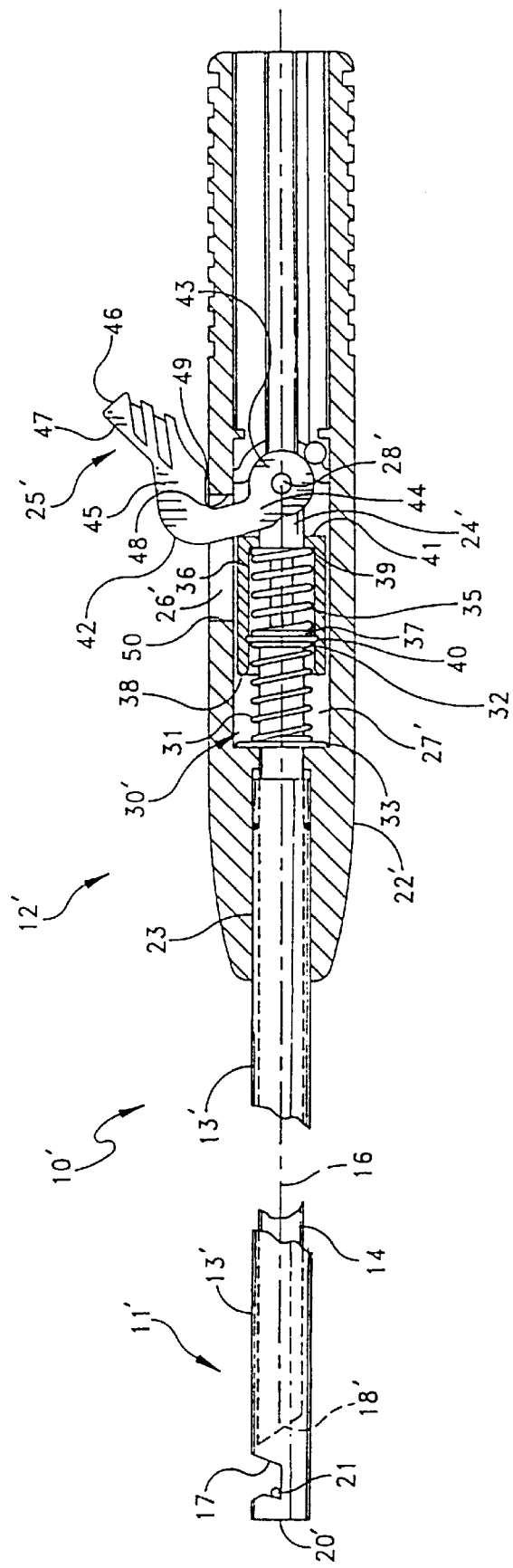

An apparatus 10' for facilitating intracorporeal suturing according to another embodiment as depicted in FIGS. 5 through 7 includes a distal section 11' and the proximal section 12'. The sheath 13' is preferably formed to be slightly longer than an underlying tubular member 14' in this embodiment and it also moves axially in response to proximal manipulation of a handle 22'. A suture needle slot 17' for receiving the suture needle 21 proximate a distal end 20' of a sheath 13'. Proximal axial displacement of the tubular member 14' as depicted in FIG. 7 releases the suture needle 21 and enables the suture needle 21 to be removed from or received in the slot 17'. On the other hand, distal axial displacement of the tubular member 14' grasps the suture needle 21 received in the slot 17' (see FIG. 6) or closes the slot and generally prevents passage of objects into the slot 17' (see FIG. 5) when no interference exists between the sheath 13' and the tubular member 14'.

The handle 22' attaches to a proximal end of the sheath 13' and supports a proximal end 24' of the tubular member 14'. A trigger 25' extends through a slot 26' in the cavity 27' in the handle 22'. The trigger 25' suitably mounted in the handle 22' moves between first and second positions as seen in FIGS. 5 and 6, respectively. A lost motion transfer assembly 30' enables the two positions of the trigger 25' to translate the tubular member 14' to its three positions. That is, as the trigger 25' moves to its distal or clockwise position, the tubular member 14' moves to the clamping position of FIG. 6, if a needle 21 is positioned in the slot 17'or to position shown in FIG. 5.

The lost motion transfer assembly 30' of FIGS. 5 through 7 includes substantially the same members as the assembly 30 of FIGS. 1 through 4. However, the distal end of the spring member 31 abuts the flange 33, which is positioned distally in the cavity 27'. Also, the proximal end of the second spring member 35 engages the now proximal end 39 of the spring cup 36 while the distal end of the second spring member 35 engages the flange 37 formed integrally with the proximal end of the tubular member 14' and positioned proximally of the central flange 32. Thus, the second spring member 35 overlies a guide tube 34 that extends distally from a proximal portion of the handle 22'. Those skilled in the art will now appreciate movement of the trigger 25' between the first and second positions enable the movement of the tubular member 14' relative to the sheath to its three positions. In the retracted position shown in FIG. 7 both springs 31 and 35 are expanded.

Figure 8:
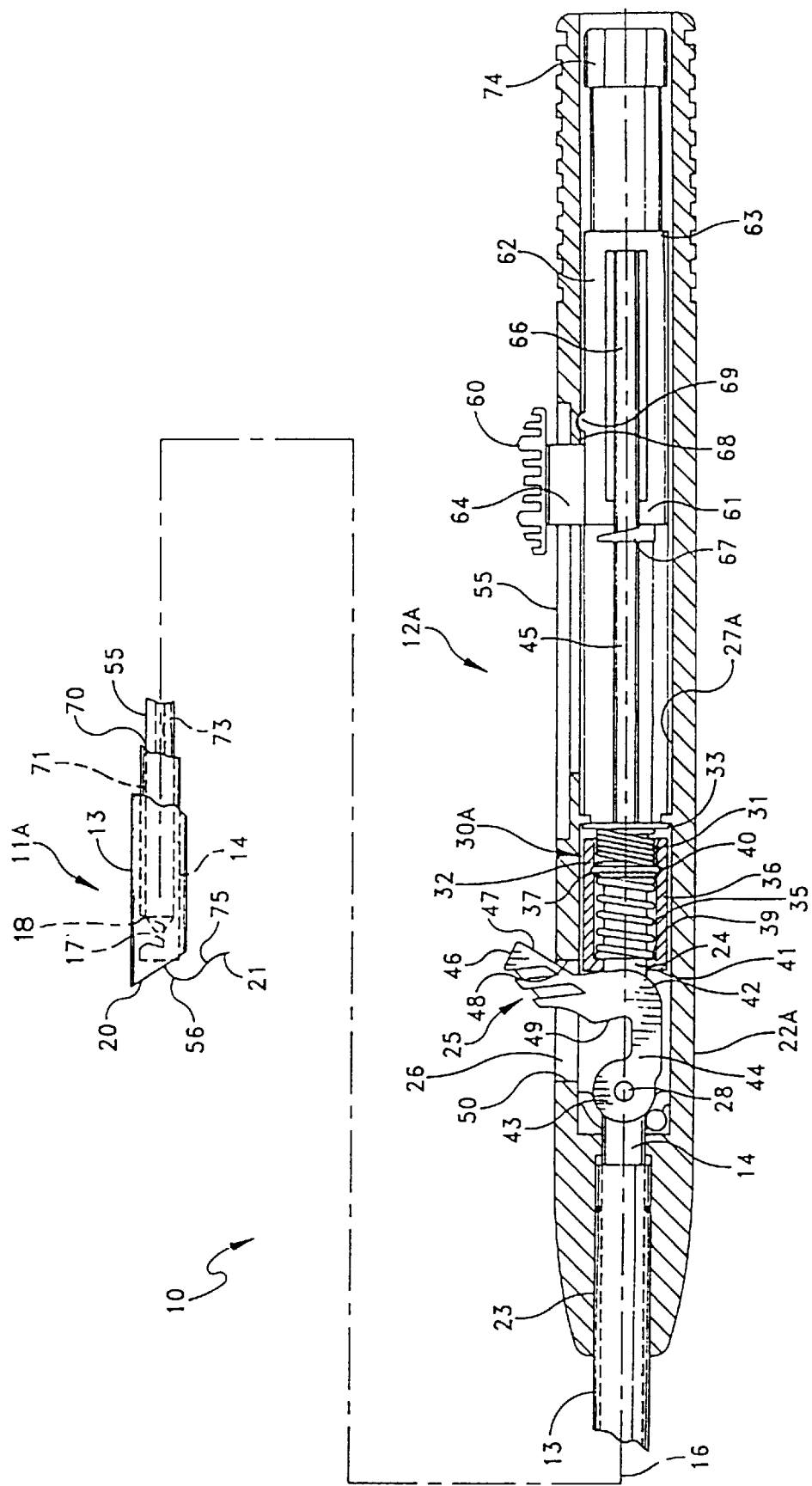
FIG. 8 is a view similar to FIG. 3, of a further embodiment of this invention.
Figure 9:
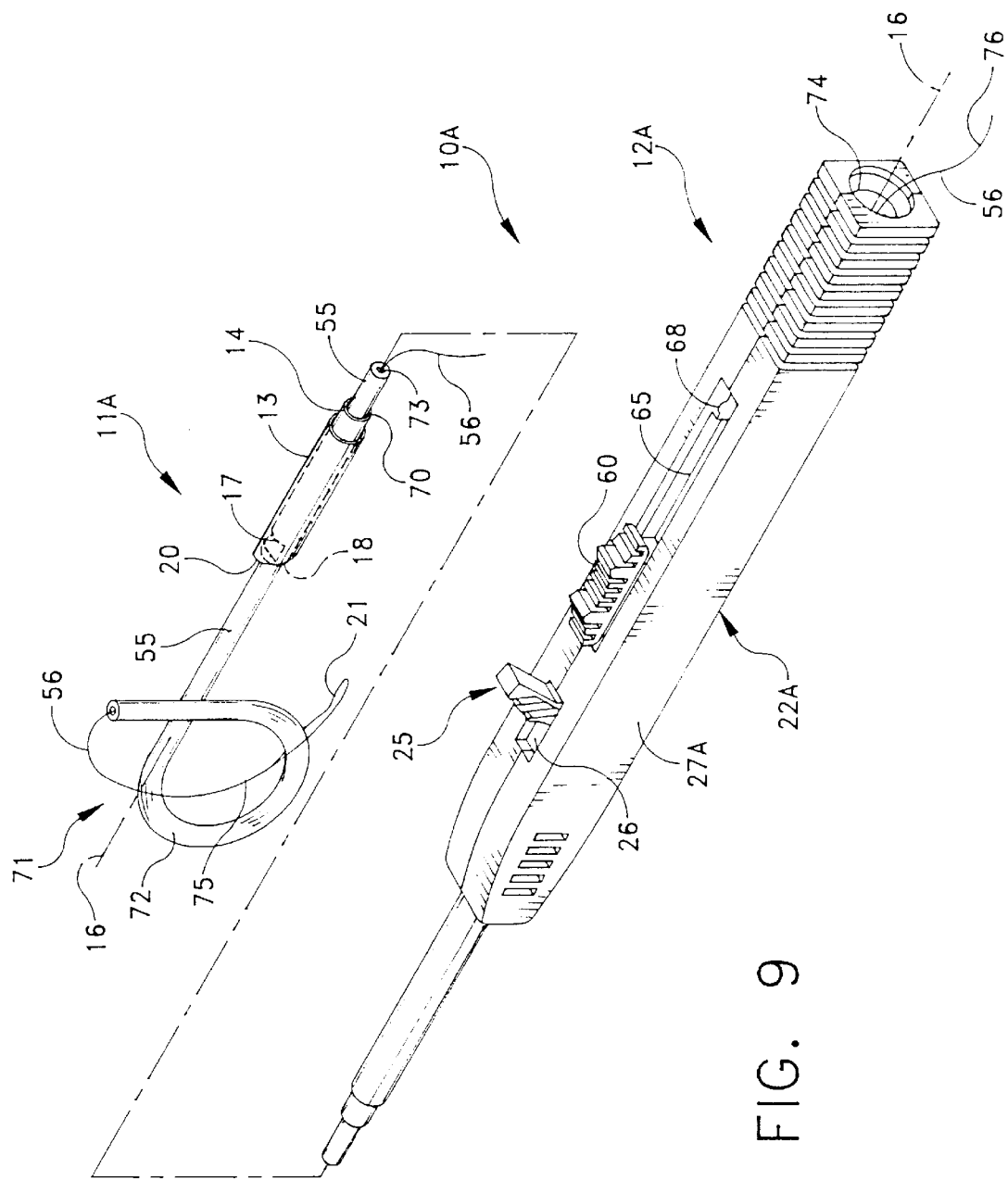
FIG. 9 is a perspective view of the embodiment of FIG. 8, with a second tubular member distally extending beyond the gripper members for facilitating intracorporeal knot tying.

Yet another needle grasping device 10A in accordance with this invention includes a proximal and distal sections 11A and 12A respectively as depicted in FIGS. 8 and 9. In FIG. 8 the gripper members, which include the slot 17 proximate the distal end 18 of the tubular member 14 and the distal end of the sheath 13, operate in substantially the same fashion as the embodiment of FIGS. 1 through 4. The distal section further includes a catheter or second tubular member 55 for facilitating intracorporeal knot tying of the suture material 56, as further explained hereinafter.

With particular reference to FIG. 8, the proximal section 12A includes a handle 22A that supports the trigger 25 for operating the gripper members and apparatus for operating the first tubular member 14 substantially as described with respect to the embodiment of FIGS. 1 through 4. A slide 60 in the handle 22A connects with a base member 61 through an arm 62 extending distally from a slidable base 63 and an upstanding member 64 extending through a slot 65 in housing 27A of the handle 22A. The housing 27A slidably supports the base member 61 within a cavity 30A defined in the housing 27A. The base member also supports a proximal end section 66 of the second tubular member 55 on a second opposed distally extending arm 67. Thus displacement of the base member 61 responsive to movement of the slide 60 within the slot 65 urges corresponding axial displacement of the second tubular member 55. The handle 22A and the base member 61 includes corresponding detent members 68 and 69 for holding the base member 61 in the proximally retracted positions as illustrated in FIG. 8.

The second tubular member 55 that extends through a passage 70 in the tubular member 14 includes a distal end portion or bight 71 that is formed of a shape memory material. Thus, upon extension the bight 71 forms the loop 72 depicted in FIG. 9 and, as the bight 71 retracts into the tubular member 14, the bight 71 assumes the linearly extending condition depicted in FIG. 8. The second tubular member 55 includes a passage or lumen 73 (FIG. 8) for receiving the suture material 56 therethrough. A seen in FIG. 9, the suture material 56 preferably extends through a gas-tight seal 74 sealing a proximal end of the housing 27A. The device 10A as depicted in FIGS. 8 and 9 thus provides apparatus for both grasping the suture needle 21 as previously described with respect to the embodiments of FIGS. 1 through 3 and FIGS. 5 through 7 and for facilitating intracorporeal knot tying as described in U.S. Pat. No. 5,447,512 to Wilson et al. which is incorporated by reference herein.

That is, after removing the suture needle 21 from the slot 17 with a free end 75 of the suture material 56 secured to the suture needle extending distally of the bight 71 of the second tubular member 55, the operator extends the second tubular member 55 by operation of the slide 60 to extend the bight 71 relative to the sheath 13 and the tubular member 14 to form the loop 72. As described in U.S. Pat. No. 5,447,512 to Wilson et al., passing the free end 75 of the suture material 53 through the loop 72 forms a loose knot. Once a loose knot is formed, the operator grasps the free end 75 of the suture material 56 with forceps or other graspers (not shown), proximally displaces the slide switch 60, and proximally retracts a proximal end 76 of the suture material to tighten the loose knot and enable thereby the operator to form a suitable overhand knot. This process can be repeated as necessary. Thus it will be understood that the device 10A enables a user to employ the devices both for suture needle grasping and for intracorporeal knot tying.

Figure 10:
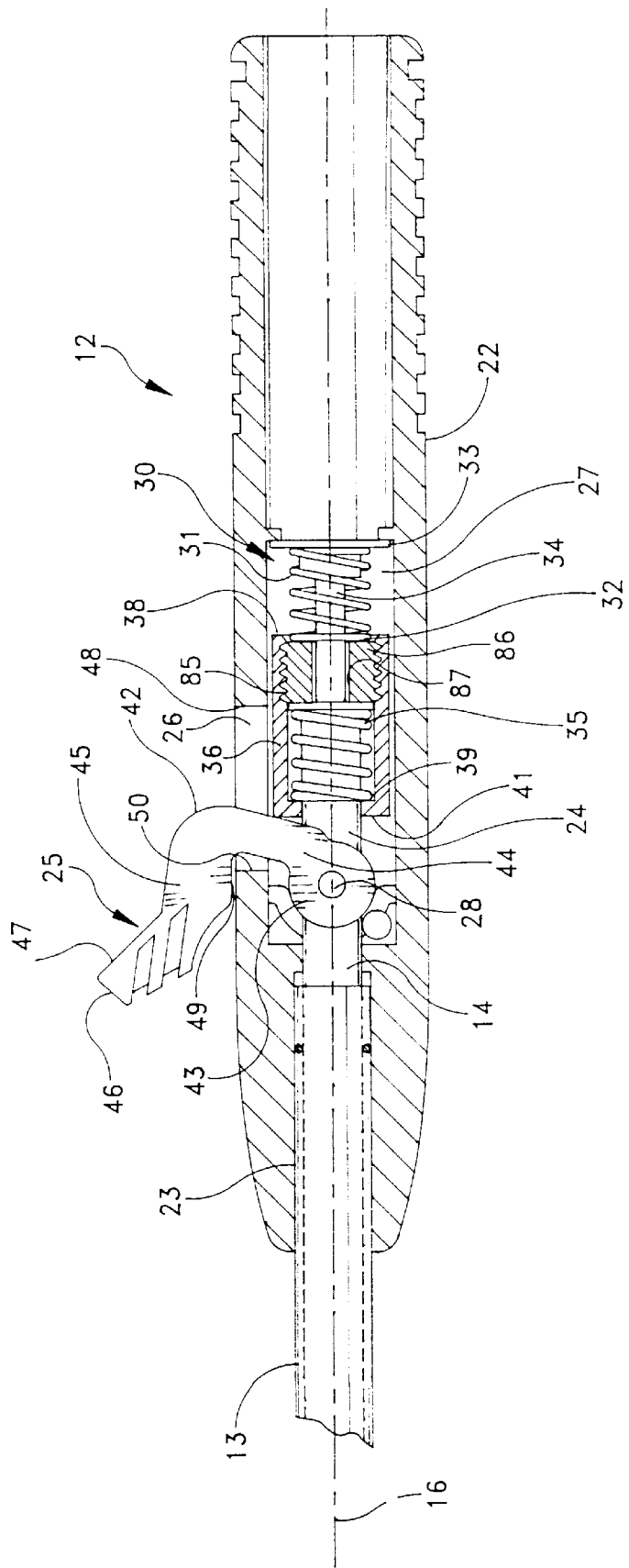
FIG. 10 is a view similar to FIG. 4 of another embodiment of the handle portion of this invention.

FIG. 10 illustrates an adjustable tension spring linkage 30 with a spring cup 36 that includes a threaded portion 85 proximally of the groove 40 for threadably engaging a tensioning member 86 that includes an aperture 87 for receiving the guide tube 34 (FIG. 1). Adjusting the screw member 86 relative to the threaded portion 85 increases or decreases the tension in the spring 35 and hence the magnitude of the clamping force at the distal end 11 (FIG. 1). Those skilled in the art will appreciate that this adjustable lost motion transfer assembly 30 can be readily substituted for the assembly 30 of FIGS. 5 through 7 or the assembly 30 of FIGS. 1 through 4.

The foregoing embodiments depicted in FIGS. 1, 5, 8 and 10 satisfy the stated objects and aims of this invention. Each provides an apparatus for facilitating a modality of endoscopic therapy that includes a handle with operator means that includes a cam for axially displacing first and second tubular members to enable the grasping release of a suture needle. A device in accordance with this invention may also include apparatus for performing a second modality of therapeutic treatment in addition to needle grasping. The operator device can include portions for controlling the second modality of therapeutic treatment including the extension and retraction of a tubular member relative to the gripping members for facilitating intracorporeal knot tying of suture material extending through the apparatus.

The disclosed embodiments also provide a control or operator device, that positively retains the distal ends of axially extending members in selected open and in intermediate and fully closed positions depending upon interference between the axially extending members. Thus, the control device of this invention, with its function to extend and its lost-motion retraction of axially extending members may be used, for example, to extend and retract relative to a sheath a retrieval basket for retrieving stones and other items. That is, the handle portion of this invention can be used with a retrieval basket such as disclosed by U.S. Pat. No. 5,496,330 to Bates et al. and commonly assigned with this invention. In such case the lost motion assembly would enable extension and retraction of the basket relative to a sheath responsive to moving the trigger between its first and second positions. Thus, upon proximal retraction of the basket relative to an outer sheath with a stone larger than the sheath, the lost motion assembly would enable the basket and stone to be retracted against the sheath. The basket with the stone would be held in this intermediate position with the trigger in its second position due to the interference between the basket and stone and the sheath.

This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A handle assembly for a surgical instrument, the surgical instrument having first and second axially, relatively displaceable members each with a proximal end, the first and second members for clamping an item that prohibits relative displacement between the first and second members, the handle assembly comprising:

a housing configured for coupling to the proximal end of the first member;

a biasing assembly configured for coupling to the proximal end of the second member, the biasing assembly having a first and a second biasing element and a casing, the casing configured for moving relative to the housing and to the second member; and a trigger movably coupled to the housing and configured to displace the casing relative to the housing, wherein the first biasing element extends between the casing and the housing and the second biasing element is configured for extending between the second member and the casing and is configured for supplying a clamping force to the item.

2. The handle assembly of claim 1 wherein the trigger is a camming device rotatably coupled to the housing.

3. The handle assembly of claim 2 wherein the first biasing element is configured for compressing upon relative movement of the casing and the first member, and the second biasing element is configured for compressing upon relative movement of the casing and the second member.

4. The handle assembly of claim 3 wherein the first biasing element is configured for biasing the distal end of the first member away from the distal end of the second member.

5. The handle assembly of claim 1 wherein the first biasing element is deflected upon movement of the trigger from a first to a second position, and the second biasing element is deflected upon movement of the trigger from the first to the second position when the item is clamped between the first and the second members.

6. The handle assembly of claim 5 wherein the first biasing element is configured for biasing the distal end of the first member away from the distal end of the second member.

7. The handle assembly of claim 1, wherein the first biasing element is configured for biasing the distal end of the second member away from the distal end of the first member, and the second biasing element is configured for biasing the distal end of the second member towards the distal end of the first member.

8. The handle assembly of claim 7 wherein the biasing assembly includes an adjustment device configured for varying the clamping force applied to the item clamped between the first member and the second member.

9. The handle assembly of claim 1, wherein the trigger has a first position an second position.

10. The handle assembly of claim 9, wherein the biasing assembly is configured to apply a first and second force to the trigger in the first and second trigger positions that maintains the trigger in the first and second trigger positions, respectively.

11. The handle assembly of claim 9, wherein in a first configuration, the trigger is in the first position and the first and second biasing elements have first and second lengths, respectively, and in a second configuration, the trigger is in the second position and the first biasing element has a third length less than the first length.

12. The handle assembly of claim 11, wherein in a third configuration resulting from an item restricting the movement of the second member relative to the first member, the trigger is in the second position, the first biasing element has the third length and the second biasing element has a fourth length less than the second length.

13. A surgical instrument having a proximal and a distal end, the surgical instrument comprising:

an elongate first member extending from the distal end to the proximal end;

an elongate second member extending from the distal end to the proximal end, the second member being axially, displaceable relative to the first member, the first and second members configured for clamping an item that prohibits relative displacement between the first and second members;

an end effector coupled to the second member at the distal end;

a housing coupled to the first member at the proximal end;

a biasing assembly coupled to the second member at the proximal end, the biasing assembly having a first and a second biasing element and a casing, the casing capable of moving relative to the housing and to the second member; and a trigger movably coupled to the housing for displacing the casing relative to the housing, wherein the first biasing element extends between the casing and the housing and the second biasing element extends between the second member and the casing and is configured to supply a clamping force to the item.

14. The surgical instrument of claim 13 wherein the trigger is a camming device rotatably coupled to the housing.

15. The surgical instrument of claim 14 wherein the first biasing element is configured to compress upon relative movement of the casing and the first member, and the second biasing element is configured to compress upon relative movement of the casing and the second member.

16. The surgical instrument of claim 15 wherein the first biasing element is configured to bias the distal end of the first member away from the distal end of the second member.

17. The surgical instrument of claim 13 wherein the first biasing element is configured to deflect upon movement of the trigger from the first to the second position, and the second biasing element is configured to deflect upon movement of the trigger from the first to the second position when the item is clamped between the first and the second members.

18. The surgical instrument of claim 17 wherein the first biasing element is configured to bias the distal end of the first member away from the distal end of the second member.

19. The surgical instrument of claim 13 wherein the biasing assembly includes an adjustment device for changing an amount of the clamping force supplied to an item that prohibits relative displacement between the first member and the second member.

20. The surgical instrument of claim 13 wherein the end effector includes a retrieval device.

21. The surgical instrument of claim 20 wherein the retrieval device includes a retrieval basket.

22. The surgical instrument of claim 13, wherein the first biasing element is configured to bias the distal end of the second member away from the distal end of the first member, and the second biasing element is configured to bias the distal end of the second member towards the distal end of the first member.

23. The surgical instrument of claim 13, wherein the trigger has a first position and a second position.

24. The surgical instrument of claim 23, wherein in a first configuration, the trigger is in the first position and the first and second biasing elements have first and second lengths, respectively, and in a second configuration, the trigger is in the second position and the first biasing element has a third length less than the first length.

25. The surgical instrument of claim 24, wherein in a third configuration, the trigger is in the second position and the first biasing element has the third length and the second biasing element has a fourth length less than the second length.

26. A handle assembly for a surgical instrument, the surgical instrument having first and second axially, relatively displaceable members each having a proximal end and a distal end, wherein relative displacement of the members defines first and second limit positions and an intermediate position for supplying a clamping load to an item interfering with the relative displacement between the members, the handle assembly configured for coupling to the proximal ends of the first and second members, the handle assembly comprising:
 a housing configured for attaching to the proximal end of the first member;
 a trigger rotatably coupled to the housing for movement between first and second trigger positions; and
 a biasing assembly configured for mounting coaxially with the members and having first and second biasing elements, the biasing assembly being responsive to motion of the trigger for permitting motion to the first limit position when the trigger is at a first trigger position and, when the trigger is at a second trigger position, for permitting motion to one of the second limit position and the intermediate position depending upon the presence of the item that prohibits relative displacement between the members.

27. The handle assembly of claim 26 wherein the biasing assembly includes a first and a second compressible spring.

28. The handle assembly of claim 27 wherein the trigger is a camming device rotatably coupled to the housing.

29. The handle assembly of claim 27 wherein the biasing assembly maintains the trigger in the first and second trigger positions.

30. A surgical instrument having a proximal and a distal end, the surgical instrument comprising:
 an elongate first member extending from the distal end to the proximal end;
 an elongate second member extending from the distal end to the proximal end, the second member being axially, relatively displaceable from the first member, the first and second members configured for clamping an item that prohibits relative displacement between the first and second members;
 an end effector coupled to the second member at the distal end;
 a housing coupled to the first member at the proximal end;
 a biasing assembly slidably coupling the housing and the proximal end of the second member, the biasing assembly having at least one biasing element and a casing capable of movement relative to both the first and second members; and
 a trigger pivotably coupled to the housing for deflecting and releasing the at least one biasing element and displacing the second member relative to the first member, wherein the trigger has a first trigger position corresponding to an extended position of the second member relative to the first member and a second trigger position corresponding to a retracted position of the second member relative to the first member.

31. The surgical instrument of claim 30 wherein the biasing assembly is configured to bias the trigger in the first trigger position to maintain the trigger in the first trigger position and to bias the trigger in the second trigger position to maintain the trigger in the second trigger position.

32. The surgical instrument of claim 31 wherein a force applied by the biasing assembly to the trigger in the first trigger position creates a moment about a trigger pivot point that maintains the trigger in the first trigger position, and a force applied by the biasing element to the trigger in the second trigger position creates a moment about the trigger pivot point that maintains the trigger in the second trigger position.

33. The surgical instrument of claim 30 wherein the biasing assembly includes first and second compressible elements.

34. The surgical instrument of claim 33 wherein the first biasing element is configured for compressing upon actuation of the trigger and displacement of the first member, and the second biasing element is configured for compressing upon actuation of the trigger and displacement of the second member.

35. The surgical instrument of claim 34 wherein the first biasing element is configured for biasing the distal end of the first member away from the distal end of the second member, and the second biasing element is configured for supplying a clamping force to the item that prohibits relative displacement between the first member and the second member.

36. A handle assembly for a surgical instrument, the surgical instrument having first and second axially, relatively displaceable members each with a proximal end, the handle assembly comprising:

a housing configured for coupling to the proximal end of the first member;

a biasing assembly configured for coupling to the proximal end of the second member, the biasing assembly having a first and a second compressible element; and a trigger coupled to the housing and configured for displacing the first member relative to the second member, wherein the trigger is a camming device rotatably coupled to the housing, and the first compressible element is configured for biasing the distal end of the first member away from the distal end of the second member and the second compressible element is configured for supplying a clamping force to an item that prohibits relative displacement between the first member and the second member.

37. A handle assembly for a surgical instrument, the surgical instrument having first and second axially, relatively displaceable members each with a proximal end, the handle assembly comprising:

a housing configured for coupling to the proximal end of the first member;

a biasing assembly configured for coupling to the proximal end of the second member, the biasing assembly having a first and a second compressible element; and a trigger coupled to the housing and configured for displacing the first member relative to the second member, wherein the biasing assembly includes an adjustment device configured for changing an amount of clamping force supplied to an item that prohibits relative displacement between the first member and the second member.

38. A surgical instrument having a proximal and a distal end, the surgical instrument comprising:

an elongate first member extending from the distal end to the proximal end;

an elongate second member extending from the distal end to the proximal end, the second member being axially, displaceable relative to the first member;

an end effector coupled to the second member at the distal end;

a housing coupled to the first member at the proximal end;

a biasing assembly coupled to the second member at the proximal end, the biasing assembly having a first and a second compressible element; and a trigger coupled to the housing for displacing the second member-relative to the first member, wherein the trigger is a camming device rotatably coupled to the housing, and the first compressible element biases the distal end of the first member away from the distal end of the second member and the second compressible element supplies a clamping force to an item that prohibits relative displacement between the first member and the second member.

39. A surgical instrument having a proximal and a distal end, the surgical instrument comprising:

an elongate first member extending from the distal end to the proximal end;

an elongate second member extending from the distal end to the proximal end, the second member being axially, displaceable relative to the first member;

an end effector coupled to the second member at the distal end;

a housing coupled to the first member at the proximal end;

a biasing assembly coupled to the second member at the proximal end, the biasing assembly having a first and a second compressible element; and a trigger coupled to the housing for displacing the second member relative to the first member, wherein the biasing assembly includes an adjustment device for changing an amount of the clamping force supplied to an item that prohibits relative displacement between the first member and the second member.

40. A handle assembly for a surgical instrument, the surgical instrument having first and second axially, relatively displaceable members each having a proximal end and a distal end, wherein relative displacement of the members defines first and second limit positions and an intermediate position for supplying a clamping load to an item interfering with the relative displacement between the members, the handle assembly configured for coupling to the proximal ends of the first and second members, the handle assembly comprising:

a housing configured for attaching to the proximal end of the first member;

a trigger coupled to the housing for movement between first and second trigger positions; and a biasing assembly configured for mounting coaxially with the members, the biasing assembly being responsive to motion of the trigger and configured for permitting motion to the first limit position when the trigger is at a first trigger position, to the second limit position when the trigger is at a second trigger position, and to the intermediate position when the trigger is at the second position and the item prohibits relative displacement between the members, wherein the trigger is a camming device rotatably coupled to the housing.

41. A surgical instrument having a proximal and a distal end, the surgical instrument comprising:

an elongate first member extending from the distal end to the proximal end;

an elongate second member extending from the distal end to the proximal end, the second member being axially, relatively displaceable from the first member;

an end effector coupled to the second member at the distal end;

a housing coupled to the first member at the proximal end;

a biasing assembly slidably coupling the housing and the proximal end of the second member, the biasing assembly having at least one compressible element; and a trigger coupled to the housing for compressing and releasing at least one compressible element and displacing the second member relative to the first member, wherein the trigger has a first trigger position corresponding to an extended position of the second member relative to the first member and a second trigger position corresponding to a retracted position of the second member relative to the first member, wherein a force applied by the biasing assembly to the trigger in the first trigger position creates a moment about a trigger pivot point that maintains the trigger in the first trigger position, and a force applied by the biasing element to the trigger in the second trigger position creates a moment about the trigger pivot point that maintains the trigger in the second trigger position.

* * * * *

UNITED STATES PATENT AND TRADEMARK OFFICE
CERTIFICATE OF CORRECTION

PATENT NO. : 6,102,920

DATED : August 15, 2000

INVENTOR(S) : Roy H. SULLIVAN et al.

It is certified that error appears in the above-identified patent and that said Letters Patent is hereby corrected as shown below:

Claim 2, column 9, line 55, before "rotatably", delete "a camming device".

Claim 9, column 10, line 19, change "position an" to --position and--.

Claim 14, column 10, line 63, before "rotatably", delete "a camming device".

Claim 19, column 11, line 18, change "claim 13" to --claim 11--;

lines 19-20, replace "changing an amount of" to --varying--;

line 20, "supplied to an" should read --applied to the--; and lines 20-21, "that prohibits relative displacement" should read --clamped--.

UNITED STATES PATENT AND TRADEMARK OFFICE
CERTIFICATE OF CORRECTION

PATENT NO. : 6,102,920

DATED : August 15, 2000

INVENTOR(S) : Roy H. SULLIVAN et al.

It is certified that error appears in the above-identified patent and that said Letters Patent is hereby corrected as shown below:

Claim 27, column 12, lines 3-4, after "wherein the", delete "biasing assembly includes a";

line 4, before "second", delete "a"; and change "compressible spring" to --biasing elements are compressible--.

Claim 28, column 12, line 6, after "camming device", delete "rotatably coupled to the housing".

Claim 33, column 12, line 51, "compressible" should read --biasing--.

Claim 38, column 13, line 50, "member-relative" should read --member relative--.

Signed and Sealed this

Twenty-fourth Day of April, 2001

Attest:

NICHOLAS P. GODICI

*Attesting Officer*    *Acting Director of the United States Patent and Trademark Office*